US00PP36398P2

(12) United States Plant Patent
Noordam

(10) Patent No.: US PP36,398 P2
(45) Date of Patent: Jan. 14, 2025

(54) ***CAMPANULA* PLANT NAMED 'CHAMELEON ROSE'**

(50) Latin Name: *Campanula medium*
Varietal Denomination: CHAMELEON ROSE

(71) Applicant: Kwekerij Stadsland, Waardenburg (NL)

(72) Inventor: Jan Noordam, Waardenburg (NL)

(73) Assignee: Kwekerij Stadsland

( * ) Notice: Subject to any disclaimer, the term of this patent is extended or adjusted under 35 U.S.C. 154(b) by 0 days.

(21) Appl. No.: 18/429,950

(22) Filed: Feb. 1, 2024

(51) Int. Cl.
*A01H 5/02* (2018.01)
*A01H 6/26* (2018.01)

(52) U.S. Cl.
USPC ..... Plt./414

(58) Field of Classification Search
USPC ..... Plt./414
CPC . A01H 5/02; A01H 5/00; A01H 6/264; A01H 6/26
See application file for complete search history.

(56) References Cited

PUBLICATIONS

Community Plant Variety Office 4.18.18 for *Campanula* 'Chameleon Rose' retrieved on Jun. 3, 2024 at https://online.plantvarieties.eu/publicConsultationDetails?registerId=20231459&denomination=chameleon%20rose, 2 pp. (Year: 2024).*

* cited by examiner

*Primary Examiner* — June Hwu
(74) *Attorney, Agent, or Firm* — Cassandra Bright

(57) ABSTRACT

A new and distinct cultivar of *Campanula* plant named 'CHAMELEON ROSE' is disclosed, characterized by biennial plants producing sterile flowers. The unique new cultivar produces unique color-changing flowers, beginning green and white, developing a pink margin with age. Flowering stems have a vase life of 20 to 22 days. Flowers on the live plants have the novel characteristic of not fading after visits by pollinators. The new cultivar is a *Campanula,* typically produced as an outdoor ornamental plant or for cut flower purposes.

2 Drawing Sheets

Figure 1:
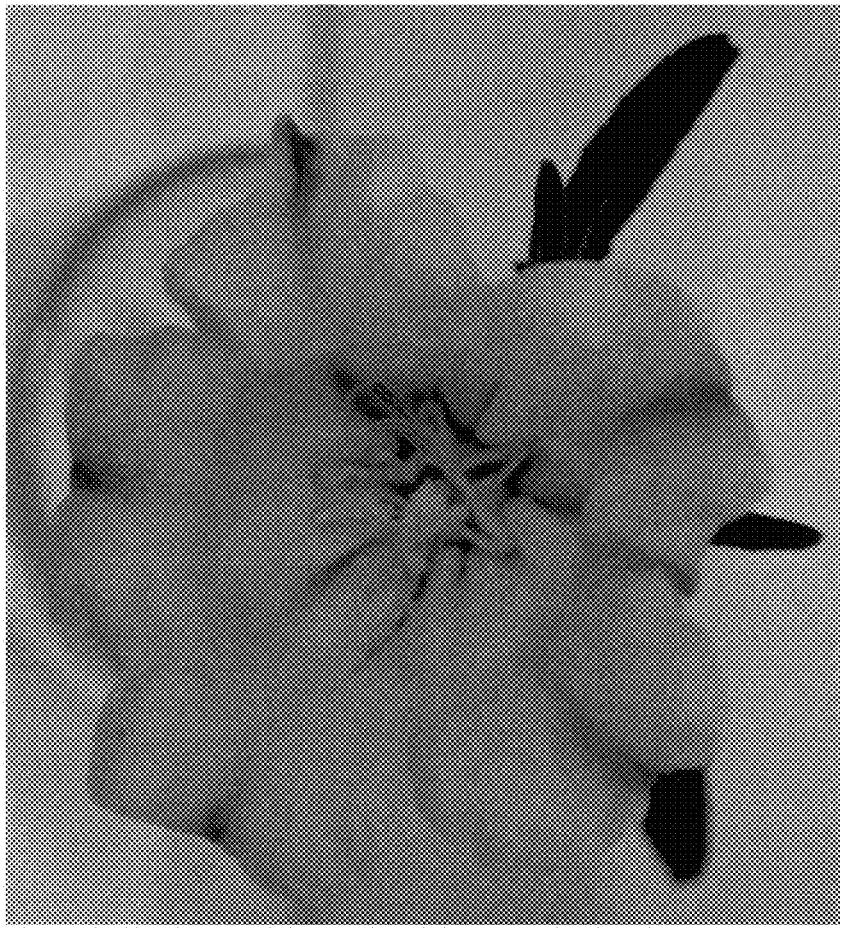

Latin name of the genus and species: *Campanula medium.*
Variety denomination: 'CHAMELEON ROSE'.

BACKGROUND OF THE INVENTION

The new cultivar is a product of a planned breeder program conducted by the inventor at a commercial nursery in Angeren, the Netherlands. The objective of the breeding program was to produce new *Campanula* varieties for both cut flower and garden use. The cross resulting in this new variety was made during June of 2019.

The seed parent is an unnamed, unpatented variety of *Campanula medium.* The pollen parent is a different unnamed, unpatented *Campanula medium.* The new variety was selected at a commercial nursery in Angeren, the Netherlands in June of 2020.

Asexual reproduction of the new cultivar 'CHAMELEON ROSE' was first performed during July of 2020 at a commercial nursery in Heerhugowaard, the Netherlands via tissue culture. Through subsequent propagation, multiple additional generations have been reproduced, having shown that the unique features of this cultivar are stable and reproduced true to type.

SUMMARY OF THE INVENTION

The cultivar 'CHAMELEON ROSE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'CHAMELEON ROSE'. These characteristics in combination distinguish 'CHAMELEON ROSE' as a new and distinct *Campanula* cultivar:

1. Sterile flowers.
2. Long lasting flowers with a vase life of 20 to 22 days.
3. Flowers do not fade after visits by pollinators.
4. Unique color change as flowers age, beginning with green and white, developing a pink petal lobe margin with age.
5. Biennial plants.
6. Multi-colored flowers of white, green, and pink.

PARENT COMPARISON

The new variety 'CHAMELEON ROSE' differs from both the seed and pollen parents in that the flowers of the new variety do not fade as occurs in both parent varieties.

COMMERCIAL COMPARISON

Plants of the new cultivar *Campanula* 'CHAMELEON ROSE' can be compared to the commercial variety *Campanula* 'Champion Pink', unpatented. Plants of 'CHAMELEON ROSE' are similar to plants of 'Champion Pink' in most horticultural characteristics, however, plants of 'CHAMELEON ROSE' differ in the following:

1. Flowers of the new variety are green, white and pink; flowers of this comparator are solid pink.
2. Flowers of the new variety do not fade after a visit by a pollinator; flowers of this comparator fade after pollination.
3. Plants of the new variety are biennial; plants of this comparator are typically grown as an annual.

Plants of the new cultivar *Campanula* 'CHAMELEON ROSE' can be compared to the commercial variety *Campanula* 'Campana Pink', unpatented. Plants of 'CHAMELEON ROSE' are similar to plants of 'Campana Pink' in most horticultural characteristics, however, plants of 'CHAMELEON ROSE' differ in the following:

1. Flowers of the new variety are green, white and pink; flowers of this comparator are solid pink.
2. Flowers of the new variety do not fade after a visit by a pollinator; flowers of this comparator fade after pollination.
3. Plants of the new variety are biennial; plants of this comparator are typically grown as annuals.

BRIEF DESCRIPTION OF THE PHOTOGRAPHS

The accompanying photograph in FIG. 1 illustrates in full color a close up a typical of 'CHAMELEON ROSE'.

Figure 2:
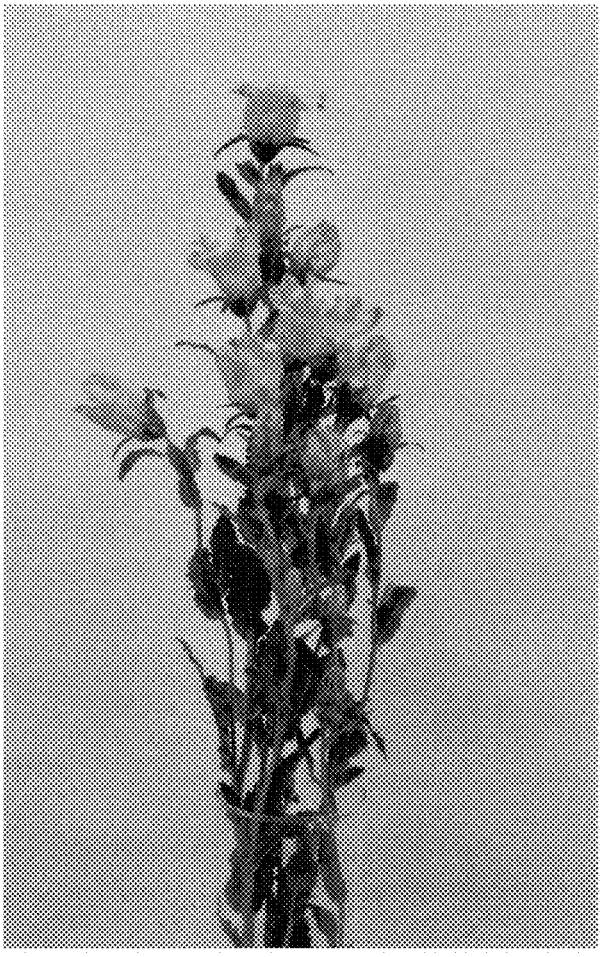

FIG. 2. Illustrates a typical flowering stem from 'CHAMELEON ROSE' grown in an unheated greenhouse in the Netherlands.

This plant is approximately 250 days old, grown in the ground. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'CHAMELEON ROSE' plants grown in the ground in an unheated greenhouse in Angeren, the Netherlands. The plants were about 250 days old. Temperatures ranged from-6° C. to 15° C. at night to 5° C. to 30° C. during the day. No chemical treatments were given to the plants, only biological control for thrips. Measurements and numerical values represent averages of typical plant types.

Botanical classification: *Campanula medium* 'CHAMELEON ROSE'.

PROPAGATION

Time to initiate roots: About 5 to 10 days at 15° C. to 20° C.

Time to produce a rooted liner: About 35 to 40 days at approximately 20° C.

PLANT

Age of plant described: Approximately 250 days.

Growth habit: Upright. Plants form a rosette before flower initiation. In Spring shoots arise from the rosette.

Height: 70 to 150 cm.

Plant spread: 40 cm.

Growth rate: Moderate.

Main stem characteristics:

Length.—Average 100 cm.

*Diameter.*—2.0 to 2.5 cm at base.

*Quantity of stems per plant.*—About 30 to 50 basally emerging stems.

*Color.*—RHS Green 140D flushed 141A.

*Texture.*—Pubescent.

*Strength.*—Very strong.

Primary lateral branches:

Quantity of primary lateral branches: 6-10.

Length of primary lateral branches: 25-40 cm.

Characteristics of primary lateral branches:

*Form.*—Round.

*Diameter.*—0.5-1 cm.

*Color.*—RHS Green 140D flushed 141B.

*Texture.*—Pubescent.

*Strength.*—Medium.

Internode length: Average range 5-7 cm.

Root description: Dense, fibrous root system. Roots variably white, not accurately measured with R.H.S. chart.

FOLIAGE

Leaf:

*Arrangement.*—At the base very crowded (rosette). On the stems alternate.

*Quantity.*—Approximately 150 to 300 per plant.

*Basal foliage.*—

*Average length.*—15 cm.

*Average width.*—3 cm.

*Shape of blade.*—Ovate-lanceolate.

*Apex.*—Acuminate.

*Base.*—Attenuate.

*Margin.*—Serrate.

*Aspect.*—Slightly undulate.

*Texture of top surface.*—Glabrous.

*Texture of bottom surface.*—Glabrous.

*Color.*—Young foliage, upper side: Near RHS Green 141D. Young foliage, under side: Near RHS Green 141D. Mature foliage, upper side: Near RHS Green 141A. Mature foliage, under side: Near RHS Green 141A.

*Venation.*—Type: Reticulate. Color, upper side: Near RHS Green 140D. Color, under side: Near RHS Green 140D.

Petiole:

*Length.*—Average 5 mm.

*Diameter.*—Average 4 mm.

*Color.*—Near RHS Green 140D flushed 141B.

*Texture.*—Glabrous.

FLOWER

Natural flowering season: May and June.

Inflorescence:

*Type and habit.*—Panicle composed of single campanulate flowers.

*Height.*—Average range 50 cm to 80 cm.

*Diameter.*—Average range 20 to 30 cm.

*Flowers per inflorescence.*—Average range 20 to 30.

Rate of flower opening: 30 to 50 days from bud to fully opened flower.

Flower longevity on plant: 30 to 40 days.

Vase life: 20 to 22 days.

Persistent or self-cleaning: Persistent.

Flower attitude: Upward.

Bud:
*Shape*.—Oval.
*Length*.—2-3 cm.
*Diameter*.—1 cm.
*Color*.—RHS Yellow-Green N144D.
Flower size:
*Diameter*.—3-4 cm.
*Depth*.—4 cm.
*Throat diameter*.—2-3 cm.
*Tube length*.—4-5 cm.
*Tube diameter at base*.—1 cm.
Petal lobes and tube:
*Petal lobes*.—Typically 5.
*Length*.—2 cm.
*Width*.—2 cm.
*Shape*.—Triangular.
*Apex*.—Rounded.
*Base*.—Fused.
*Curvature*.—Moderately reflexing.
*Texture, outer surfaces*.—Petal Lobe: Soft, glabrous. Tube: Soft, glabrous.
*Texture, inner surfaces*.—Petal Lobe: Soft, glabrous. Tube: Soft, glabrous. Throat: Soft, glabrous.
*Color*.—Outer Surfaces: Petal Lobe when opening: RHS Green-White 157B, center streak Yellow-Green 145A margin very faintly flushed Red-Purple 69A. Tube when opening: RHS Green-White 157A, center streak Yellow-Green 145A very faintly flushed Red-Purple 69A. Petal Lobe fully opened: RHS White 155C, center streak Yellow-Green 145A margin flushed Red-Purple 69A. Tube fully opened: RHS Green-White 157D, center streak Yellow-Green 145A margin flushed Red-Purple 69A. Inner Surfaces: Petal Lobe when opening: RHS Green-White 157D, center streak Yellow-Green 145A margin faintly flushed Red-Purple 69A. Tube when opening: RHS Green-White 157B, center streak Yellow-Green 145A. Throat when opening: RHS Yellow-Green 145A. Petal Lobe fully opened: RHS White 155C, center streak Yellow-Green 145A, margin flushed Red-Purple 69A. Tube fully opened: RHS Green-White 157D, center streak Yellow-Green 145A. Throat fully opened: RHS Green-White 157A, center streak Yellow-Green 145A. Petal Lobe fading: RHS Yellow-Green 145A. Tube fading: RHS Yellow-Green 145A. Throat fading: RHS Yellow-Green 145A. Presence of dots on inner or outer corolla tube: None.
Sepals:
*Position of the calyx lobes to the corolla*.—Moderately spreading.
*Quantity*.—5.
*Length*.—1.5-2 cm.
*Width*.—1 cm.
*Shape*.—Ovate.
*Apex*.—Acuminate.
*Base*.—Obtuse.
*Margin*.—Serrate.
*Texture*.—Outer Surface: Pubescent, almost bristly. Inner Surface: Smooth.
*Color*.—Outer Surface: RHS Yellow-Green 144C. Inner Surface: RHS Yellow-Green 145A.
Calyx Petaloid Lobes: None.
Peduncles:
*Length*.—1-2 cm.
*Diameter*.—3 mm.
*Angle*.—About 60° to the lateral branch.
*Strength*.—Medium.
*Texture*.—Pubescent.
*Color*.—RHS Yellow-Green 145A.
Pedicels:
*Length*.—1-2 cm.
*Diameter*.—3 mm.
*Angle*.—About 60° to the lateral branch.
*Strength*.—Medium.
*Texture*.—Pubescent.
*Color*.—RHS Yellow-Green 144C.

REPRODUCTIVE ORGANS

Stamens:
*Number per flower*.—Typically 5.
*Filament length*.—1 cm.
*Filament color*.—Near RHS White 155C.
Anthers:
*Shape*.—Linear.
*Length*.—3 mm.
*Color*.—Near RHS White 155C.
*Pollen*.—Scant. Colored near Yellow 5B. Non-viable.
*Pistil*.—
*Quantity per flower*.—1.
*Length*.—Approximately 2 to 3 cm.
*Style*.—Length: Approximately 2 cm. Color: Near RHS White 155D.
*Stigma*.—Shape: Orbicular. Color: Yellow 2B.

OTHER CHARACTERISTICS

Disease/pest resistance: Neither resistance nor susceptibility to common diseases and pests of *Campanula* has been observed.
Temperature tolerance: Zone 8 hardiness.

What is claimed is:

1. A new and distinct cultivar of *Campanula* plant named 'CHAMELEON ROSE' as herein illustrated and described.

* * * * *